(12) United States Patent
Chen et al.

(10) Patent No.: US 11,136,696 B2
(45) Date of Patent: Oct. 5, 2021

(54) EXTRUSION PROCESS FOR MANUFACTURING OF ABSORBABLE SUTURE FIBERS

(71) Applicant: Ethicon, Inc., Somerville, NJ (US)

(72) Inventors: Gaoyuan Gavin Chen, Hillsborough, NJ (US); Joseph Richard Vliet, Jr., Califon, NJ (US); Dominick Egidio, Flanders, NJ (US)

(73) Assignee: Ethicon, Inc., Somerville, NJ (US)

( * ) Notice: Subject to any disclaimer, the term of this patent is extended or adjusted under 35 U.S.C. 154(b) by 212 days.

(21) Appl. No.: 16/183,861

(22) Filed: Nov. 8, 2018

(65) Prior Publication Data

US 2020/0149194 A1    May 14, 2020

(51) Int. Cl.
    *D01F 8/14*      (2006.01)
    *D01D 4/02*      (2006.01)
    *D01D 5/08*      (2006.01)
    *A61B 17/06*     (2006.01)
    *C08L 67/04*     (2006.01)

(52) U.S. Cl.
    CPC .......... *D01F 8/14* (2013.01); *A61B 17/06166* (2013.01); *D01D 4/02* (2013.01); *D01D 5/08* (2013.01); *C08L 67/04* (2013.01)

(58) Field of Classification Search
    CPC .... D01F 8/14; D01F 6/84; D01D 4/02; D01D 5/08; B29C 48/873; B29C 48/802; B29C 2948/92704; B29C 2948/92209; B29C 48/92; B29C 48/022; B29C 48/05; B29K 2995/006; B29K 2067/046; B29K 2995/0056; A61B 17/06166
    See application file for complete search history.

(56) References Cited

U.S. PATENT DOCUMENTS

| 5,516,815 A |   | 5/1996  | Buehler |
|---|---|---|---|
| 5,718,716 A | * | 2/1998  | Goddard ................ A61L 17/12 |
|             |   |         | 264/210.7 |
| 6,005,019 A | * | 12/1999 | Liu ........................ A61L 17/12 |
|             |   |         | 523/105 |
| 6,007,565 A | * | 12/1999 | Roby ...................... A61L 17/12 |
|             |   |         | 606/228 |

(Continued)

FOREIGN PATENT DOCUMENTS

| EP | 1375706 B1   | 1/2008  |
|----|--------------|---------|
| WO | 02090627 A1  | 11/2002 |

*Primary Examiner* — Jeffrey M Wollschlager
(74) *Attorney, Agent, or Firm* — David R. Crichton (57) ABSTRACT

A novel process is disclosed for extruding an absorbable glycolide/lactide block copolymer into multifilament suture fibers. The block copolymer preferably consists of about 50/50 mole % of Glycolide/Lactide in the center segment and the overall composition of the copolymer is about 90/10 mole % Glycolide/Lactide. The novel extrusion process comprises the steps of maintaining the temperatures of at least two, preferably three or more, of the extrusion zones in the range of about 5-50° C. below the polymer melting point. The multifilament suture made with the invention process from the segmented, glycolide-rich, poly(glycolide-co-lactide) copolymers of A-B-A type, where the B-segment is an amorphous prepolymer of glycolide and lactide in the molar ratio of about 50/50 glycolide/lactide, exhibit exceptionally high breaking strength retention (BSR) at 42 days post-implantation.

13 Claims, 5 Drawing Sheets

Schematic extrusion setup of the current invention.

(56) References Cited

U.S. PATENT DOCUMENTS

| | | | |
|---|---|---|---|
| 6,147,135 A * | 11/2000 | Yuan | A61F 2/30965 |
| | | | 523/105 |
| 7,378,045 B2 | 5/2008 | Chen | |
| 7,738,045 B2 | 6/2010 | Doswald | |
| 2003/0186008 A1 * | 10/2003 | Sutton | C08J 5/18 |
| | | | 428/36.9 |
| 2004/0098049 A1 * | 5/2004 | Im | A61L 17/12 |
| | | | 606/230 |
| 2005/0171250 A1 | 8/2005 | Hayes | |
| 2012/0190597 A1 * | 7/2012 | Chatterjee | B82Y 30/00 |
| | | | 507/269 |
| 2020/0181018 A1 * | 6/2020 | Caviezel | B32B 13/12 |

\* cited by examiner

Figure 1. Schematic extrusion setup of the current invention.

Figure 2. Melting Point ($T_m$) vs. Mole % Lactide in Center Block of Gly/Lac Copolymers Having about 90 mole % Glycolide in Overall Composition.

Mole % Lactide in Center Block of 90/10 Gly/Lac Copolymers

Figure 3. Fiber Tenacity of Trial I Examples vs. Extrusion Conditions of a 90/10 Gly/Lac with Center Block of 50% Lactide (PG910C50) Block Copolymer having 1.31 dL/g IV.

Figure 4. Example II Fiber Tenacity vs. Extrusion Conditions of PG910C50 Copolymer having 1.29 dL/g IV.

Figure 5. Example III Fiber Tenacity vs. Extrusion Conditions of PG910C50 Copolymer having 1.52 dL/g IV.

EXTRUSION PROCESS FOR MANUFACTURING OF ABSORBABLE SUTURE FIBERS

FIELD OF INVENTION

This invention relates to a novel extrusion process for manufacturing absorbable multifilament fibers from a semi-crystalline segmented, glycolide-rich, poly(glycolide-co-lactide) block copolymer to make absorbable braided sutures having high initial breaking strength and enhanced breaking strength retention post-implantation.

BACKGROUND OF THE INVENTION

Manufacturing process for making sutures from synthetic absorbable polyesters are well known in the art. Absorbable sutures generally come in two basic forms, multifilament braids and monofilaments. Absorbable multifilament sutures made from glycolide (Gly) homopolymer and glycolide/lactide (Gly/Lac) copolymers are commercially available such as Coated VICRL', which is widely used for soft tissue closure.

To ensure there are adequate support during the wound healing process, it is critical to have a high enough initial tensile strength and sufficiently long breaking strength retention (BSR) with an absorbable suture until the wound is essentially healed, which usually takes about 3-6 weeks, depending on the type of wound or patient.

It has been known to a skilled person in the art that the BSR or its profile may be altered by changing the composition and/or chemical structure of absorbable polymers. It is also known that the initial breaking strength of a braided suture depends mainly on the fiber tenacity as the total amount of fibers used is constrained by the braid construction and the USP (United States Pharmacopeia) limits on suture diameters for a given suture size. Tenacity is the customary measure of strength of a fiber or multifilament yarn. It is usually defined as the maximum breaking force in grams (abbreviated g) divided by the denier. Denier (abbreviated d) is a unit of measure for the linear mass density of fibers, which is the mass in grams per 9000 meters of a fiber or multifilament yarn. Hence, the tenacity unit of a fiber or yarn is usually expressed in [g/d].

To help improve the fiber tenacity, hence the suture breaking strength, U.S. Pat. No. 7,738,045 taught a unique extrusion temperature profile for 90/10 mole % Glycolide/Lactide random copolymer, which has a melting point of about 200° C. By the prior art teaching, the temperature of at least one of the 3 extruder zones (i.e., feed, transition and metering zones) should be kept relatively low, preferably no more than 5° C. above the polymer melting point, the temperature of the subsequent pump and block zones should be gradually increased, but no more than 40° C. above the polymer melting point, and the temperature of the spinneret should be quickly raised to about 40-60° C. above the polymer melting point. Under the optimized temperature profile according to the prior art, the fiber tenacity of over 7.2 g/d, up to as high as 7.9 g/d, was achieved from 90/10 mole % Gly/Lac random copolymer.

One shortcoming of the known commercially available absorbable multifilament sutures made from glycolide-rich (about 90/10 mole %) Lac/Gly random copolymers is that the BSR drops to essentially zero in about 5 weeks after implantation. Sutures having longer BSR would be beneficial when closing wounds for patients having compromised healing, such as diabetic patients, geriatric patients, and possibly patients under chemotherapy.

Longer-term absorbable multifilament suture is also known and has been made from lactide-rich polymers, such as 95/5 Lac/Gly copolymer, which requires about 18-30 months to be absorbed. This suture material is not absorbed by the body within an optimal time frame. Therefore, there is a need for an absorbable multifilament suture that exhibits high initial tensile strength, long breaking strength retention (BSR) extended over about 6 weeks for slow wound healing applications and yet absorbs in a relatively short time, preferably in 18 weeks or less.

Applicants discovered that multifilament suture made from a semi-crystalline segmented, glycolide-rich, poly(glycolide-co-lactide) copolymers of A-B-A type, where the B-segment is an amorphous prepolymer of glycolide and lactide in the molar ratio of about 50/50 glycolide/lactide, and wherein the total amount of polymerized glycolide is about 88 to about 92 mole-% of said absorbable copolymer, exhibit exceptionally high BSR at 42 days post-implantation.

When the above segmented A-B-A block Gly/Lac copolymer was extruded with a R&D extruder, a mean tenacity as high as about 8.0 g/d was readily achieved under the optimized conditions. However, when the extrusion was conducted in a manufacturing plant, some difficulties were encountered to produce fibers having an individual spool average tenacity consistently meeting the proposed Lower Specified Limit (LSL) of 5.6 g/d or meeting the target of 6.0 g/d mean tenacity using the teaching of the preferred temperature profile taught in U.S. Pat. No. 7,738,045 or using other extrusion conditions commonly known in the art.

In an R&D/laboratory setting, extruded molten filaments are normally quenched by the ambient air where there is only one extruder running for trial that may last for just a few hours. The total distance from the spinneret surface to the $1^{st}$ take-up godet can be about 17 feet, which is believed to be sufficiently long enough for the extruded filaments to become solidified before being converged and wound up. In the extrusion room of a production plant, there could be ten or more extruders running simultaneously 24 hours day, 7 days a week (24-7). The production extruders are usually individually isolated with a safety enclosure below each extruder to minimize undesirable air motions that may disturb the extruded molten filaments, the ambient air surrounding the molten filaments inside the chimney and cooling stack may contain a relatively high concentration of evaporated glycolide and lactide monomers, which may slow down the cooling efficiency of the molten filaments and/or cause more severe thermal degradation of the polymer. Besides, the total stack distance from spinneret to the $1^{st}$ take-up godet is limited to only about 12 feet in the manufacturing site due to floor space limitations, which is about 5 feet shorter than that of the R&D extruder. The difference in cooling stack distance may lead to some additional difference in cooling and or spinning tension profiles, which in turn may yield extrudate fiber morphology somewhat different from that made with the R&D extruder setup under optimized conditions for achieving the best tenacity in the oriented fibers.

The process of the current invention addresses the above problem encountered in manufacturing the absorbable multifilament suture fibers from the segmented glycolide/lactide block copolymers in a production plant. As will be described in further detail hereinafter, the present invention discloses a unique combination of extrusion process steps for manufacturing absorbable multifilament suture fibers from the segmented glycolide/lactide block copolymers, which resulted in sufficiently high fiber tenacity and exceptionally high breaking strength retention (BSR) profile for an extended period up to 42 days after implantation.

SUMMARY OF THE INVENTION

A novel process is disclosed for extruding an absorbable glycolide/lactide copolymer into multifilament suture fibers with high tenacity in a manufacturing plant. The block copolymer preferably consists of about 50/50 mole % of Gly/Lac in the center segment and the overall composition of the copolymer is about 90/10 mole % Gly/Lac. The novel extrusion process comprises the steps of maintaining the temperatures of at least two, preferably three or more, of the extrusion zones in the range of about 2-50° C. below the polymer melting point.

Applicants discovered that the multifilament suture made with the invention process from the segmented, glycolide-rich, poly(glycolide-co-lactide) copolymers of A-B-A type, where the B-segment is an amorphous prepolymer of glycolide and lactide in the molar ratio of about 20/80 to about 70/30 glycolide/lactide, exhibit exceptionally high BSR at 42 days post-implantation.

One aspect of the present invention is that absorbable multifilament fibers having a spool average tenacity of 5.6 g/d or higher can be readily produced in a manufacturing environment using the segmented Gly/Lac block copolymers, wherein inherent viscosity (IV) of the polymer can be as low as about 1.2-1.3 dL/g.

Another aspect of the present invention is an absorbable multifilament suture made from the segmented Gly/Lac block copolymers of a relatively wide range of 1.2-1.6 dL/g having a BSR of 10% or more at 42 days post-implantation and yet absorbs in a relatively short time, approximately 18 weeks or less.

These and other aspects and advantages of the present invention will become more apparent from the following description and accompanying figures.

DETAILED DESCRIPTION OF THE INVENTION

Figure 1:
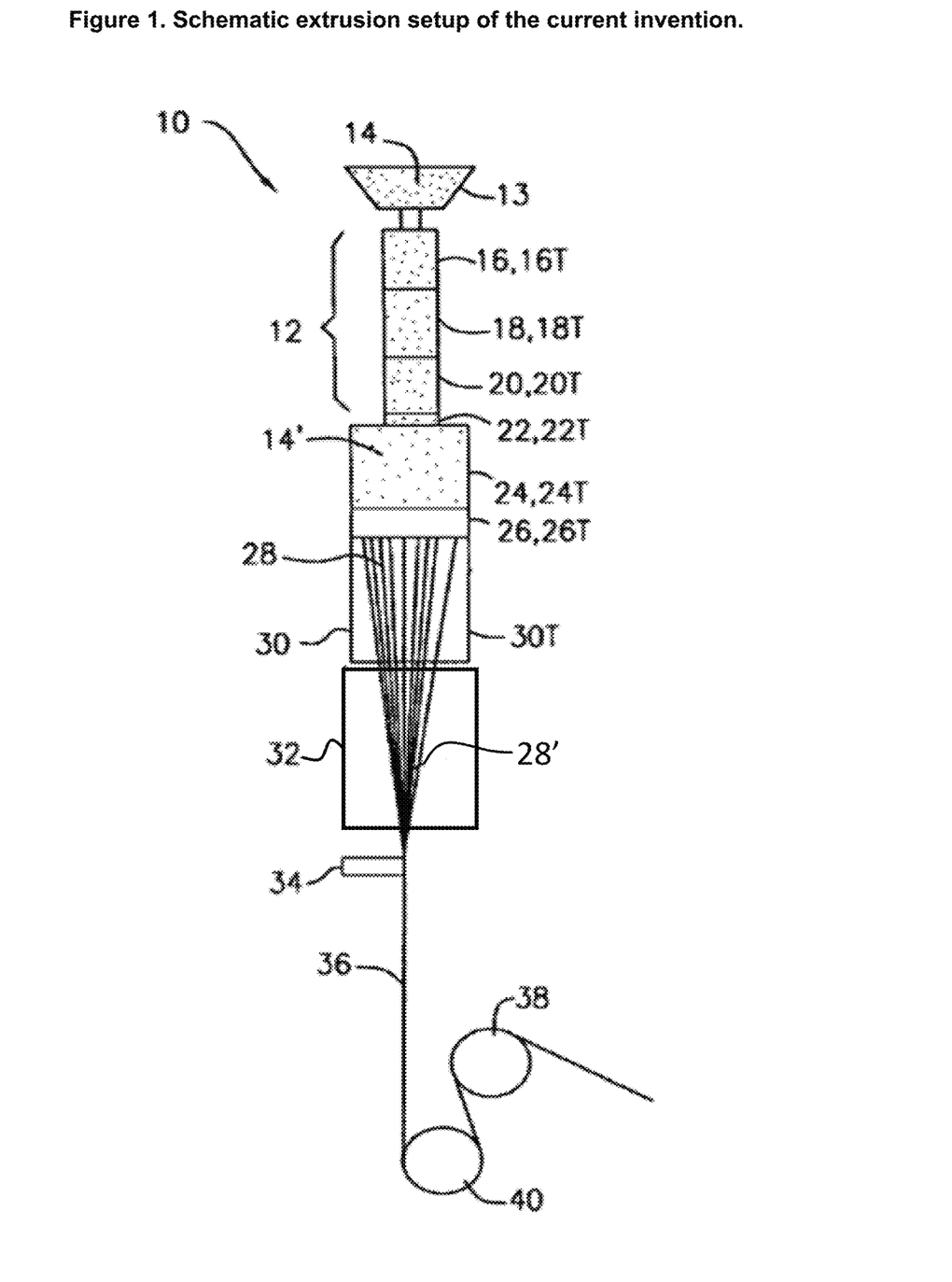
FIG. 1. Schematic extrusion setup of the current invention.

For a better understanding of the present invention, reference is made to the following detailed description of a preferred embodiment of the present invention considered in conjunction with the accompanying drawings. FIG. 1 provides a schematic representation of the extruder apparatus 10 that is utilized for manufacturing multifilament fibers of this invention. More particularly, the extruder apparatus 10 has sequentially arranged interconnected components, including a polymer feeding means, such as hopper 13, and an extruder barrel 12 that is located substantially vertically beneath the hopper 13. The hopper 13 holds and feeds the dried polymer pellets 14 into the extruder barrel 12. The feed hopper is usually filled with inert gas such as Nitrogen to avoid or minimize moisture absorption from air by the polymer. The hopper may also be kept cold by running chilled water through the outer shell of the hopper feed section to keep the polymer from being pre-heated/softened in the hopper.

The extruder barrel 12 includes three sequentially arranged heated zones 16, 18, 20, which are maintained at a certain preferred temperature profile for efficient heating, feeding and forcing the copolymer pellets 14 into a flowable melt stream 14', as discussed in further detail hereinafter in connection with the process of the present invention. A metering pump 22 is positioned at or near the end of extruder 12. A heated block 24 is connected to metering pump 22. The metering pump 22 controls the rate at which the polymer melt stream 14' is pumped into block 24. The extruder barrel, and metering pump may be positioned vertically or horizontally next to each other or in any way suitable for extruding and metering the polymer flow.

Spinneret 26 is located substantially vertically beneath block 24 and has a plurality of capillary orifices (not shown). The polymer melt 14' is pumped through the spinneret 26, under high pressure in the block 24 to form multiple molten filaments 28, as will be described hereinafter. The block 24 may include a series of fine screen filters and breaker plates (not shown) to achieve and maintain a consistency of the polymer melt 14' that is extruded through the spinneret 26.

With continued reference to FIG. 1, a heated sleeve 30 of about 6-20 inches is attached to, and extends substantially vertically beneath, the spinneret 26 for delaying the cooling of the extruded molten filaments 28 before entering the ambient cooling zone 32. The heated sleeve 30 is usually made of solid metal such as a steel or aluminum tube, which are heated to desirable temperature with band or cartridge heaters. The heated sleeve may also be referred to as "Chimney" because there is usually some smoking coming out at the exit of the heated sleeve 30. The smoking is formed by the evaporation of residual glycolide and/or lactide monomers left in the dried polymer after polymerization and/or formed due to thermal degradation during extrusion. The molten filaments exiting the chimney are then cooled down naturally by the surrounding air in ambient cooling zone 32, which is confined within a metal tube extending from about 0.5 inches below the chimney 30 to about 1-2 feet above the finish applicator 34. In the manufacturing environment, there is usually an openable safety enclosure (not shown) surrounding the chimney 30 and the upper portion of inter-floor tube 32 to minimize undesirable air movement in the operation room, which otherwise may cause undesirable disturbance of the molten filaments. The enclosure may be made of any sheet metal with some openable slots or perforations to allow the vaporized monomers (the smoke) to escape and some ambient cooling air to enter from the top of the inter-floor tube 32.

A spin finish applicator 34 is positioned at about 1-2 feet below the inter-floor tube 32 and applies a lubricating spin finish (not shown) to the supposedly solidified filaments 28', after which the cooled filaments 28' converge into a bundle 36. The bundled filaments 36 are passed through take-up godet rolls 38, 40, and wound up by a winder (not shown). The distance from spinneret 26 to the take-up godet roll 40 is about 12 feet for the manufacturing extruders. The said bundled filaments then undergo further processing, including, but not necessarily limited to, drawing and orienting with conventional drawing apparatus (not shown). The oriented multifilament yarn is then wound up again with a winder. The spools of oriented fibers are then tested before being braided to make braided sutures.

It is noted that all the above-described components of the extruder apparatus 10 shown schematically in FIG. 1 are generally conventional components that are typically known to those having ordinary skill in the art and which are readily available from any known commercial sources. More particularly, a suitable extruder barrel 12 and a suitable heated block 24 can be obtained from Davis-Standard, Pawcatuck, Conn. In addition, a suitable metering pump 22 may be available from Zenith Pump Division, Sanford, N.C. Suitable spinnerets 26 and heated sleeves 30 can be obtained from AUTRANS Corp., Farmington Hills, Mich. 48331. Similarly, a suitable spin finish applicator 36 could be obtained from Slack & Parr, Inc., Charlotte, N.C.

In addition, although not shown, the above-described extruder apparatus 10 must include appropriate heating and temperature control devices. As will be obvious to one of ordinary skill in the art, heating devices are required to heat each of the various above-described heated components to the desired temperatures (which will be discussed in detail hereinafter). The temperature control devices are necessary to detect and maintain the temperatures of the components within the predetermined desired ranges in accordance with the present invention. Such heating and temperature control devices are also well-known and readily available from commercial sources, including, but not limited to, Honeywell Inc., Fort Washington, Pennsylvania.

The process of the present invention includes operation of the above-described extruder apparatus 10 such that a temperature profile is created from the heated zones 16, 18, 20 of the extruder barrel 12, to the spinneret 26, to the temperature of the heated sleeve 30, as will be discussed hereinafter. To facilitate discussion and illustration of the aforesaid temperature profile, the temperature of each of the heated components of the extruder apparatus 10 will hereinafter be referred to by using a temperature label composed of its reference number and the letter "T" thereafter. For example, the temperature of the first heated zone 16 of the extruder barrel 12 will be referred to hereinafter using the temperature label 16T and the temperature of the spinneret 26 will be referred to hereinafter using the temperature label 26T. The temperature labels are noted, for reference, in FIG. 1.

Furthermore, it is noted that suitable temperatures for the heated components of the extruder apparatus 10 will depend upon the melting point temperature of the polymer pellets 14 that are used. Therefore, suitable temperatures for the heated components of the extruder apparatus 10 will be discussed in terms relative to the melting point of the polymer pellets 14.

With reference still to FIG. 1, in a conventional melt extrusion process of fibers, typical temperatures of the extrusion zones from feed 16, to spinneret 26 are set near or usually at least several degrees above the melting point of the polymer with either a relatively flat or increasing profile. As a rule, the process temperatures before or at the spinneret are about 50° C. above the melting point (ref. page 215, Chris Rauwendaal, <<Polymer Extrusion>>, Second, Reprinted Ed., Hanser Publishers, 1990).

In U.S. Pat. No. 7,378,045, where a random copolymer of Glycolide/lactide was extruded into multifilament fibers, it was found that by keeping one or more of the three extruder zones around or even a few degrees below the melting point of the polymer were preferable in order to obtain fibers with higher tenacity while the temperatures of the pump 22 and block 24 were kept in the range of 0-40° C., and the spinneret 26 kept at least 40° C. above the polymer melting point.

While the preferred temperature profiles of the prior art teaching might be suitable for some absorbable polymers such as 90/10 mole-% random Gly/Lac copolymer, we have found that it is difficult or sometimes impossible to produce suture fibers that can meet the desirable mean tenacity target and/or consistently exceeds the minimum product spec limit for tenacity in a manufacturing environment from an A-B-A type block copolymer, where the center block B consists of about 50/50 mole % Glycolide/Lactide with an overall composition of about 90/10 mole % Gly/Lac. For simplicity, this block polymer may be referred to as PG910050 hereinafter.

Through this invention, we have surprisingly discovered a new unique extrusion temperature profile that can enable the production of absorbable multifilament fibers from PG910050 that can consistently meet the proposed mean target of 6.0 g/d, and/or exceed the lower spec limit (LSL) of 5.6 g/d for individual fiber spool average tenacity in a manufacturing environment. In accordance with the present invention, the feeding temperature 16T of the first heated zone 16 of the extruder barrel 12 is preferably kept in the range of about 20 to 50° C. below the melting point of the polymer. The temperature in transition zone 18, metering pump 22 and the block 24 need to be kept as low as possible. Preferably two of the three temperatures of 18T, 22T & 24T are kept in the range of 3 to 20° C. below the polymer melting point. The temperature in the transition zone 18 or metering zone 20 of the extruder is preferably kept in the range of about −5 to about +5° C. from the polymer melting point. The temperature of the spinneret 26 should also be kept relatively low, preferably in the range of −10 to +10 from the polymer melting point.

The temperature of the heated sleeve 30, which is not in direct contact with the polymer or filaments, is not critical but is preferably set at about 50° C. above the polymer melting point, whereby the extruded molten filaments 28 will be maintained in a hot environment for ease of attenuation before being exposed to ambient cooling air. As discussed hereinabove, the length of the heated chimney 30 is preferably between approximately about 5 to 20 inches. After the filaments 28 pass through and emerge from the heated sleeve 30, they are cooled down by the surrounding ambient air within a proper enclosure and/or through an inter-floor tube and undergo further processing steps described previously hereinabove.

The result of utilizing the above-described process, which creates the above-discussed temperature profile, is the production of absorbable fibers from PG910050 block copolymer that can be drawn into multifilament yarn of 20 to 100 deniers. The multifilament yarn made under the process conditions of this invention with PG910050 block copolymer possesses an individual fiber spool average tenacity of at least 5.6 g/d and a mean tenacity of about 6.0 g/d or higher for a production lot or sample set under a given set of preferred extrusion conditions. The braided suture made from the said multifilament yarn has breaking strength retention (BSR) of 10% or more at 42 days post-implantation and yet absorbs in a relatively short time, approximately 18 weeks or less.

The process of the present invention is particularly suitable to produce multifilament yarns from absorbable PG910050 block copolymer of relatively low inherent viscosity of about 1.20-1.40 dL/g. As the inherent viscosity increases, the viscosity of the polymer melt usually increases. This may require slightly higher temperature in the spinneret and/or other extrusion zones. However, it is still preferable to keep the temperatures of two or more of the extrusion zones, preferably the feeding and transition zones in the range of 5-30° C. below the melting point, and the spinneret temperature not to exceed 30° C. above the melting point of PG910050 polymer having relatively high IV ranging from 1.4-1.6 dL/g.

The inherent viscosity (IV) of the polymer can be measured in hexafluoroisopropanol at 25° C. and at a concentration of 0.10 g/dL. The polymer melting point can be determined by Differential Scanning calorimetry (DSC) using the first heat scan with a heating rate of 10° C./min.

It is well known in the literature that the polymer melting point depends strongly on the composition or mole-% glycolide in Glycolide/Lactide copolymers. For example, according to D. K. Gilding and A. M. Reed, biodegradable polymers for use in surgery-polyglycolic/poly (lactic acid) homo- and copolymers: 1. Polymer 1979 20 (12), 137-143, the melting point of 90/10 mole % Gly/Lac random copolymer is about 200° C., which is consistent with what was reported in U.S. Pat. No. 7,378,045.

Figure 2:
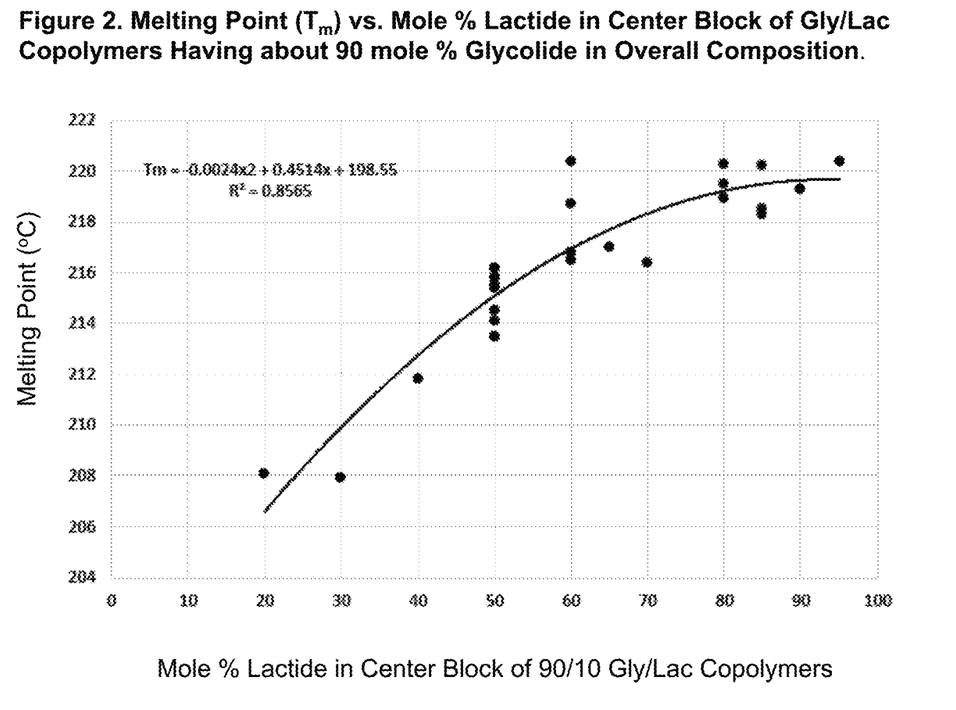
FIG. 2. Melting Point ($T_m$) vs. Mole % Lactide in Center Block of Gly/Lac Copolymers Having about 90 mole % Glycolide in Overall Composition.

For a given overall composition of 90/10 mole-% Gly/Lac A-B-A block copolymers, however, we have found that the melting point can be influenced significantly by the mole % of Lactide in the center block B, which is shown in FIG. 2.

The melting data shown in FIG. 2 were obtained with a TA Instruments Differential Scanning calorimeter, Model 2910 MDSC, using dry $N_2$ as a purge gas. Typically, about 5-10 mg of a polymer resin was placed in an aluminum pan, secured by a lid (cover), and positioned in the autosampler holder area of the instrument. The polymer specimen was first quenched to −40° C., followed by the constant heating rate at 10° C./min up to 260° C. The peak melting temperature of the first heat scan data, which are indicative of "as is" properties of the dried polymer resin before extrusion, was taken as the melting point of the polymer used in FIG. 2 and wherever it is referred to in this invention.

Based on the regression formulation in FIG. 2, the melting point ($T_m$) of 90/10 Gly/Lac block copolymer may be calculated with equation (1) below for any given mole % Lactide (X) in the center block B:

$$T_m = 198.55 + 0.4514X - 0.0024X^2 \qquad (1)$$

For example, with mole % Lactide X of 50% in the center block, the melting point of PG910050 is calculated to be 215.1° C. This calculated value is very close to the average melting point of 214.8° C. tested on numerous PG910050 polymer samples synthesized under a variety of polymerization conditions (The standard deviation of the melting point was 0.98° C. among the 68 PG910050 samples produced under various polymerization conditions). This observation suggested that the melting point of a 90/10 Gly/Lac block copolymer can be increased by about 15° C. compared to that of 90/10 Gly/Lac random copolymer, which is about 200° C. as discussed above.

The melting point of PG901050 block copolymer was found to be little or not significantly influenced by polymerization process variables such as the ratio of monomer to catalyst, or monomer to initiator. For example, when the monomer to initiator ratio was varied from 550:1 to 900:1, which resulted in polymer IV change from about 1.29 to about 1.53 dL/g, the melting point measured by DSC hardly deviated from the mean of about 215° C. calculated using Eq. (1). Based on the about observation, a nominal average melting point of 215° C. will be used hereinafter as the reference point for establishing the preferred temperature specifications for extruding PG910050 block copolymer.

According to the current invention, the preferred extrusion temperature specifications are summarized in the Tables 1 and 2:

TABLE 1

Preferred Extrusion Temperature Ranges of this Invention for PG910C50 Block copolymers having melting point of about 215° C.

| Polymer IV Range (dL/g) | Low (1.3 ± 0.1) | High (1.5 ± 0.1) |
| --- | --- | --- |
| Extruder Feed Zone Temp. (° C.) | 165 - 190 | 175 - 200 |
| Transition Zone Temp.(° C.) | 185 - 205 | 195 - 210 |
| Metering Zone Temp.(° C.) | 190 - 220 | 220 - 235 |
| Pump Zone Temp.(° C.) | 185 - 210 | 210 - 240 |
| Block Zone Temp.(° C.) | 185 - 210 | 210 - 240 |
| Spinneret Zone Temp.(° C.) | 201 -215 | 215 - 250 |

TABLE 2

Preferred Degrees of Extrusion Temperatures ($T_{ex}$) below (−) or above (+) the Polymer Melting Point ($T_m$).

| Polymer IV Range (dL/g) | Low (1.3 ± 0.1) | High (1.5 ± 0.1) |
| --- | --- | --- |
| Preferred Number of Extrusion Zones below $T_m$ | >=4 | >=2 |
| Extrusion Zones | ($T_{ex}$ - $T_m$ ° C.) | ($T_{ex}$ - $T_m$ ° C.) |
| Feed Zone | (−45) to (−25) | (−30) to (−5) |
| Transition Zone | (−30) to (−5) | (−30) to (−5) |
| Metering Zone | (−5) to (+5) | (+5) to (+30) |
| Pump Zone | (−15) to (−5) | (+10) to (+20) |
| Block Zone | (−20) to (−5) | (+10) to (+20) |
| Spinneret Zone | (−6) to (+5) | (+15) to (+30) |

Note that, although the melting point was not influenced much by the IV of the polymer, the melt viscosity does increase significantly when the polymer IV increases. It is preferable to increase the temperatures by 10-15° C. in one or more of the extrusion zones when the polymer IV exceeds 1.4 dL/g or higher.

During the scale-up polymerization runs of PG910050 block copolymer in a production plant, it was found that there are about half or more of the polymer lots showing polymer IV in the relatively low range of about 1.3+0.1 dL/g. The preferred extrusion specifications proposed in Tables 1 and 2 were based on the actual extrusion runs using the two different levels of polymer IVs, one around 1.3 and the other around 1.5 dL/g, which will be described later in detail through Examples of extrusion trials I, II and III.

The multifilament extrudates are preferably wound up at a fixed speed of about 1730 fpm. The multifilament extrudates were drawn in a subsequent step with a total draw ratio in the range of 4-6 (more preferably about 5.0X) on conventional drawing equipment such as Killion drawing stands. The denier per filament (dpf) of the drawn fibers is preferably in the range of 1.5 to 2.5 dpf (more preferably about 2.0 dpf). The temperature of the orientation roll (i.e., the roll feeding the undrawn filaments) is preferably in the range of 70-90° C., and the temperature of the drawing roll (also often referred to as the annealing roll) is preferably in the range of 90-130° C. The number of filaments in a yarn bundle can be varied from as few as 4 to as many as 50. The total denier of the oriented yarn may vary from 8 to 100. The low specified limit (LSL) for individual fiber spool average tenacity is 5.6 g/d to produce multifilament yarns for making absorbable braided suture. The fiber spool average property is obtained by testing 15 yarn specimen taken from the same spool of fibers. To minimize waste due to rejection of fibers that fails to meet the minimum tenacity requirement, it is preferable to keep the mean tenacity of all the samples produced within a given lot or a given set of conditions at 6.0 g/d or higher.

Denier may be determined by using any conventional denier wheel with meter counter and an analytical balance. Tensile properties of multifilament yarn can be tested on Textechno Statimat ME or ME+ tensile tester with a gauge length of 50 cm and a strain rate of 72 cm/min.

The braided sutures made from the fibers of PG910050 block copolymers extruded under the preferred processing conditions of this invention was found to have surprisingly high in vitro breaking strength retention (% BSR). The %-BSR was still as high as about 80% at 21 days and 15% or more at 42 days in vitro.

The in vitro BSR measurements were conducted at physiologically relevant in vitro conditions: 7.27 pH buffer solution maintained at 37° C. temperature. The data was used for BSR evaluations in pounds and percentages. At specified time points, the tensile strength of samples was tested using an Instron material testing machine. The test parameters were 1.0-inch gauge length and 1.0 inch per minute cross-head speed.

For those skilled in the art to better understand or practice the teaching of the unique process of this invention described herein, the following examples are provided as an illustration of how to determine the setpoints or specs of extrusion process to manufacture multifilament yarns from PG910050 block copolymer for making braided absorbable sutures having desirable fiber tenacity and a high level of in vitro BSR. It should be noted that the invention is not limited to the specific composition of 90/10 mole % Gly/Lac block copolymer embodied in the examples. The novel extrusion temperature profile of this invention may be used also for extrusion of other type of absorbable polymers that may readily undergo thermal degradation and/or transesterification when they are melted and kept at high temperatures above the melting point of the polymers during the extrusion steps.

Extrusion Trial I Examples

A PG910050 block copolymer (i.e., 90/10 mole % Gly/Lac block copolymers with a center block of about 50 mole % Gly/Lac) having an IV=1.31 dL/g and a melting point of about 215° C. was extruded on a 1" vertical extruder. The extrusion setup is illustrated in FIG. 1. Detailed extrusion procedure has been specified hereinabove. The temperature settings are shown in Tables 3 and 4.

TABLE 3

Temperature Set-Points for Extrusion of PG910C50 Block Copolymer having IV of 1.31 dL/g.

| Extrusion Trial I | Examples | | | | | | |
|---|---|---|---|---|---|---|---|
| Sample Set | A | B | C | D | E | F | G |
| Feed Temp. (° C.) | 180 | 180 | 170 | 180 | 180 | 180 | 180 |
| Transition Temp. (° C.) | 210 | 210 | 210 | 205 | 205 | 205 | 205 |
| Metering Temp. (° C.) | 230 | 220 | 215 | 220 | 220 | 220 | 220 |
| Pump Temp. (° C.) | 230 | 220 | 215 | 210 | 205 | 205 | 210 |
| Block Temp. (° C.) | 230 | 220 | 215 | 210 | 205 | 205 | 210 |
| Spinneret Temp. (° C.) | 235 | 225 | 220 | 215 | 210 | 210 | 215 |
| Chimney Temp. (° C.) | 285 | 285 | 285 | 285 | 285 | 273 | 280 |
| No. of Fiber Spools | 3 | 5 | 5 | 3 | 4 | 3 | 11 |
| Pump Pressure Ave. (psi) | 1593 | 2056 | 2305 | 2564 | 2823 | 2925 | 2696 |
| Tenacity Mean (g/d) | 5.56 | 5.65 | 6.01 | 6.47 | 6.52 | 6.66 | 6.47 |
| Elongation Mean (%) | 22.2 | 20.7 | 21.9 | 20.6 | 21.1 | 20.0 | 20.5 |

TABLE 4

Preferred Degrees of Extrusion Temperatures ($T_{ex}$) below (−) or above (+) the Polymer Melting Point ($T_m$).

| Extrusion Trial I | Examples | | | | | | |
|---|---|---|---|---|---|---|---|
| Sample Set | A | B | C | D | E | F | G |
| Feed Zone | −35 | −35 | −45 | −35 | −35 | −35 | −35 |
| Transition Zone | −5 | −5 | −5 | −10 | −10 | −10 | −10 |
| Metering Zone | 15 | 5 | 0 | 5 | 5 | 5 | 5 |
| Pump Zone | 15 | 5 | 0 | −5 | −10 | −10 | −5 |
| Block Zone | 15 | 5 | 0 | −5 | −10 | −10 | −5 |
| Spinneret Zone | 20 | 10 | 5 | 0 | −5 | −5 | 0 |

The extruded multifilament yarns were then drawn on conventional Killion orientation stands in a manufacturing plant. The extruded filaments were drawn into oriented fibers with orientation roll temperature of 84±5° C., annealing roll temperature of 115±10° C. and a total draw ratio of about 5.0.

Figure 3:
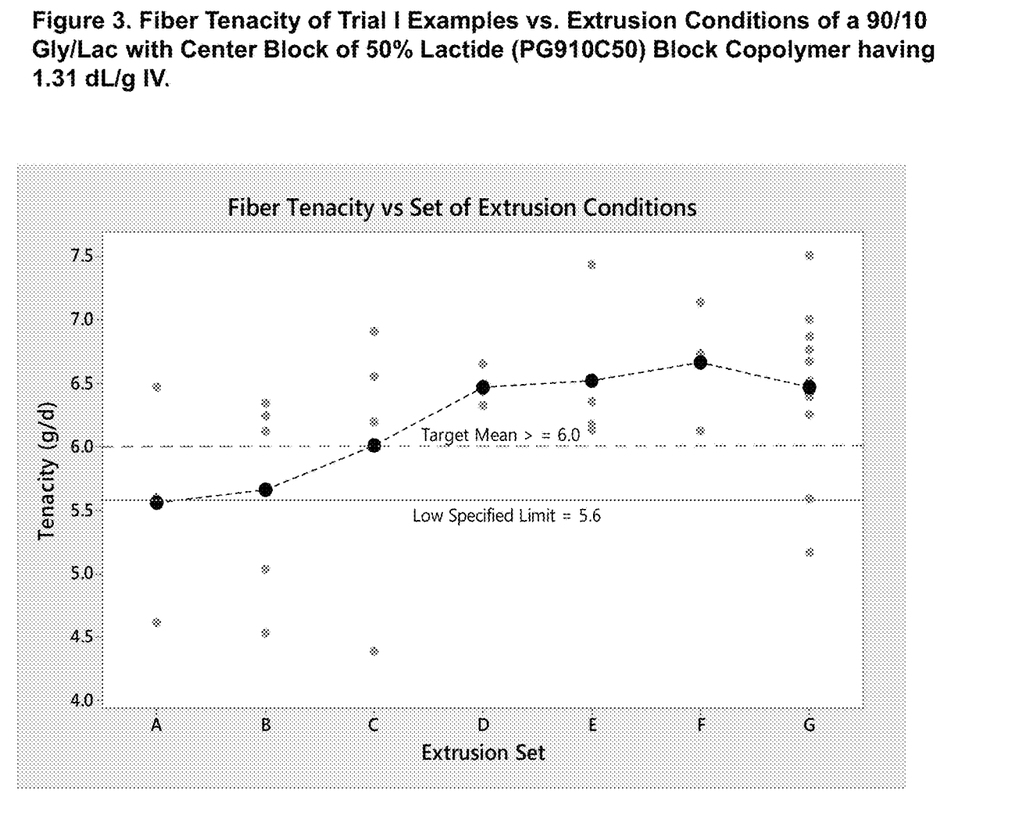
FIG. 3. Fiber Tenacity of Trial I Examples vs. Extrusion Conditions of a 90/10 Gly/Lac with Center Block of 50% Lactide (designated as PG910050) Block Copolymer having 1.31 dL/g IV.

The individual spool average tenacity is shown in FIG. 3 for each set of samples corresponding to the extrusion temperatures listed in Tables 3 and 4. With the first set of condition A where the temperature of the metering zone to spinneret zones were kept at 230-235° C., which is about 15-20° C. above the polymer melting point, the fiber tenacity was very low; more than half of the samples had individual spool average tenacity that failed to meet the proposed lower specified limit (LSL) of 5.6 g/d and the mean tenacity of the set was significantly below the preferred target mean of 6.0 gpd.

With conditions B where the pump, block and die temperatures were dropped to just a few degrees (only about 4 to 9° C.) above the polymer melting point, the fiber tenacity did not seem to improve much; two of the five samples failed to meet the tenacity LSL and the mean tenacity was still significantly below the proposed minimum target of 6.0 g/d.

In condition C where pump and block were dropped to 215° C., about the same as the polymer melting point (T$_m$), and the die was only about 5° C. above T$_m$, most (4 out of 5) samples showed tenacity above the LSL of 5.6 g/d, with one tenacity being still below the LSL. The mean tenacity just met the minimum target mean of 6.0 gpd. In the conventional fiber extrusion processes, extruding a polymer at or so close to the melting point is unusual and might be very difficult or impossible to produce useful fibers continuously.

However, we were very surprised that, with condition D where the temperature in the pump and the block zone were decreased to 5° C. below the polymer melting point, and the die temperature was also dropped to about −1° C. from the MP of the polymer, it was still possible to continuously extrude the polymer and produce good quality multifilament extrudates with the PG910050 block copolymer with relatively low IV of 1.31 dL/g. There were no issues encountered either when the multifilament extrudates were produced under the unusually cold extrusion temperatures, or when the extrudates were drawn 5 times as usual on the drawing stands. All of the oriented fiber spools passed the low specified tenacity limit of 5.6 g/d. The mean tenacity of the set reached about 6.5, well exceeding the minimum target mean of 6.0 g/d.

Following the above surprising finding, we dropped the temperatures in pump, block and spinneret zones by 5 more degrees in condition E, which corresponding to about 10° C. below the melting point in the pump and block zones, and about 5° C. below melting point in the spinneret zone. Surprisingly again, the process of extruding the polymer 5-10 below the melting point was still very stable. After being drawn 5 times as usual with no issues, the tenacity of the oriented samples of conditions E all passed the LSL of 5.6 gpd and the mean tenacity remained at about 6.5 gpd. In condition F, the extrusion temperature profile was kept the same as in E, but the chimney temperature was decreased 15° C. from a usual setpoint of 285 to 273° C. The mean tenacity increased a little bit to 6.6 gpd while elongation mean dropped from about 21% to 20%, which is still within the preferred specs range of 15-30%.

The extrusion trials were run continuously for 2-3 hours under each of the first 5 conditions from set A to F and 3-5 oriented fiber spools were produced. To demonstrate and verify process stability over an extended period, extrusion temperatures of condition D was repeated in Set G with a minor change (5° C. lower) in the chimney zone. Extrusion was run continuously for over 8 hours and 11 oriented fiber spools were produced. The pump pressure remained steady in the range of 2600 to 2730 psi, well below the operational limit of 7500 psi maximum. The mean tenacity of the 11 samples of set G was again about 6.5 gpd, same as that of Set D. Ten of the eleven samples passed or exceeded the tenacity LSL of 5.6 g/d; only one sample failed due to some unknown variation or noises occurring in processing or testing, which is not uncommon in a manufacturing process.

Extrusion Trial II Examples

Figure 4:
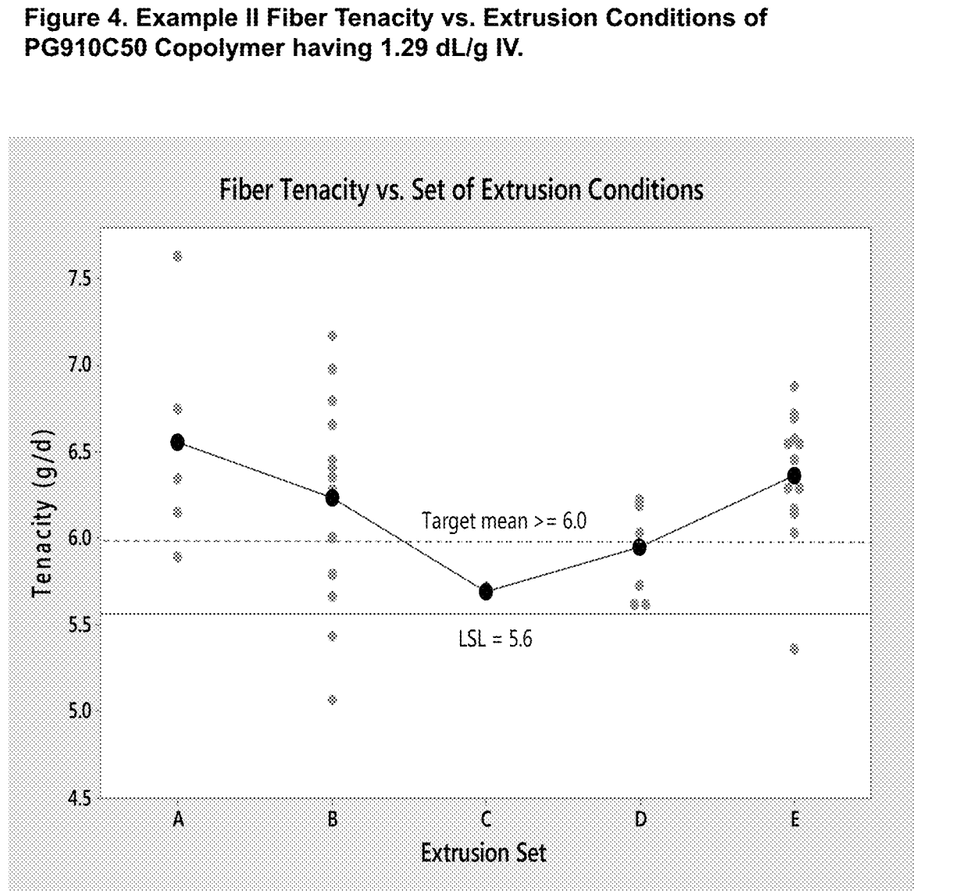
FIG. 4. Fiber Tenacity of Trial II Examples vs. Extrusion Conditions of PG910050 Copolymer having 1.29 dL/g IV.

The extrusion trial II was run on the same extrusion equipment as in Trial I but with a different PG910050 polymer lot having an IV of 1.29 dL/g and a melting point of about 215° C. The trial began with Set A conditions, which were the same as that of Trial I Set G. Four other sets of different extrusion conditions, as listed in Tables 5 and 6, were then evaluated for process suitability and the resulting fiber properties. The orientation conditions were the same as Trial I. The individual spool average tenacity of the samples is shown in FIG. 4 for each set of extrusion conditions.

TABLE 5

Temperature Set-Points for Extrusion of PG910C50 Block Copolymer having IV of 1.29 dL/g.

| Extrusion Trial II | Examples | | | | |
|---|---|---|---|---|---|
| Sample Set | A | B | C | D | E |
| Feed Temp. (° C.) | 180 | 180 | 175 | 175 | 175 |
| Transition Temp. (° C.) | 205 | 204 | 185 | 185 | 185 |
| Metering Temp. (° C.) | 220 | 218 | 200 | 215 | 215 |
| Pump Temp. (° C.) | 210 | 210 | 210 | 200 | 200 |
| Block Temp. (° C.) | 210 | 210 | 210 | 200 | 200 |
| Spinneret Temp. (° C.) | 215 | 218 | 218 | 210 | 215 |
| Chimney Temp. (° C.) | 280 | 280 | 280 | 280 | 280 |
| Total Samples | 5 | 13 | 3 | 7 | 13 |
| Pump Pressure Ave. (psi) | 2598 | 2573 | 2652 | 3090 | 2921 |
| Tenacity Mean (g/d) | 6.56 | 6.24 | 5.70 | 5.95 | 6.37 |
| Elongation Mean (%) | 20.6 | 20.5 | 21.4 | 22.8 | 21.4 |

TABLE 6

Preferred Degrees of Extrusion Temperatures (T$_{ex}$) below (−) or above (+) the Polymer Melting Point (T$_m$).

| Extrusion Trial II | Examples | | | | |
|---|---|---|---|---|---|
| Sample Set | A | B | C | D | E |
| Feed Zone | −35 | −35 | −40 | −40 | −40 |
| Transition Zone | −10 | −11 | −30 | −30 | −30 |
| Metering Zone | 5 | 3 | −15 | 0 | 0 |
| Pump Zone | −5 | −5 | −5 | −15 | −15 |
| Block Zone | −5 | −5 | −5 | −15 | −15 |
| Spinneret Zone | 0 | 3 | 3 | −5 | 0 |

This trial showed that the temperature profile of Set A is most preferable for the relatively low IV polymer as the mean tenacity reached 6.6 gpd, and all individual spool average tenacity passed the minimum requirement of 5.6 gpd. Conditions of B, D and E were also acceptable as the mean tenacity was at or above the preferred minimum target mean of 6.0 gpd, and most of the individual spool average tenacity data (except two in Set B, and one in Set E) passed the low specified limit of 5.6 gpd. All three samples of Set C also had spool average tenacity exceeding the low specified limit of 5.6 gpd, but the mean tenacity was slightly lower than the preferred target minimum of 6.0 gpd probably because the metering zone temperature at 15° C. below melting point was a little bit too low considering the two prior zones, feed and transition temperatures, were even colder, at 30-40° C. below the melting point. It is preferable to have one of the three extruder zones, preferable the metering zone, set at a temperature at or slightly above the melting point to cause sufficient melting and flowability of the polymer. After the metering zone, it is preferable to keep the pump and block temperatures 5 to 16° C. below the polymer melting point to minimize transesterification and thermal degradation for the PG910050 block copolymers having relatively low IV.

Extrusion Trial III Examples

Extrusion Trial III was conducted on the same manufacturing equipment as in Trials I and II using PG910050 block copolymer but having a relatively high IV of 1.52 dL/g. Although the melting point is not significantly influenced by the IV of the polymer, the melt viscosity seems increased significantly with the polymer IV, which is evidenced by significant increase in the pump pressure required to push the melt flow through the spinneret if the extrusion temperature is not properly adjusted. Due to this consideration, we started the extrusion (Set A and B in Tables 7 and 8) of the high IV polymer with pump and block temperatures set at about 20° C. above, and spinneret temperature about 30° C. above the polymer melting point of 215° C. The pump pressure was kept in the range of about 2200 to 2500 psi and the extrusion process was stable during the trial run extending over 24 hours.

TABLE 7

Extrusion Variables and Properties of Trial III Fiber Examples Made with 50G/50L CB 90PGA/10PLA Copolymer having 1.52 dL/g IV

| Extrusion Trial III | Examples | | |
|---|---|---|---|
| Sample Set | A | B | C |
| Feed Temp. (° C.) | 180 | 180 | 180 |
| Transition Temp. (° C.) | 210 | 210 | 210 |
| Metering Temp. (° C.) | 230 | 230 | 230 |
| Pump Temp. (° C.) | 235 | 235 | 230 |
| Block Temp. (° C.) | 235 | 235 | 230 |
| Die Temp. (° C.) | 245 | 245 | 235 |
| Chimney Temp. (° C.) | 280 | 285 | 285 |
| Total Samples | 2 | 4 | 18 |
| Pump Pressure Ave. (psi) | 2386 | 2182 | 2421 |
| Tenacity Mean (g/d) | 5.92 | 6.03 | 6.57 |
| Elongation Mean (%) | 21.2 | 20.5 | 22.5 |

TABLE 8

Degree of Extrusion Temperature below (−) or above (+) Polymer Melting Point ($T_{ex} - T_m$, ° C.)

| Extrusion Trial III | Examples | | |
|---|---|---|---|
| Sample Set | A | B | C |
| Feed Zone | −35 | −35 | −35 |
| Transition Zone | −5 | −5 | −5 |
| Metering Zone | 15 | 15 | 15 |
| Pump Zone | 20 | 20 | 15 |
| Block Zone | 20 | 20 | 15 |
| Die Zone | 30 | 30 | 20 |

Figure 5:
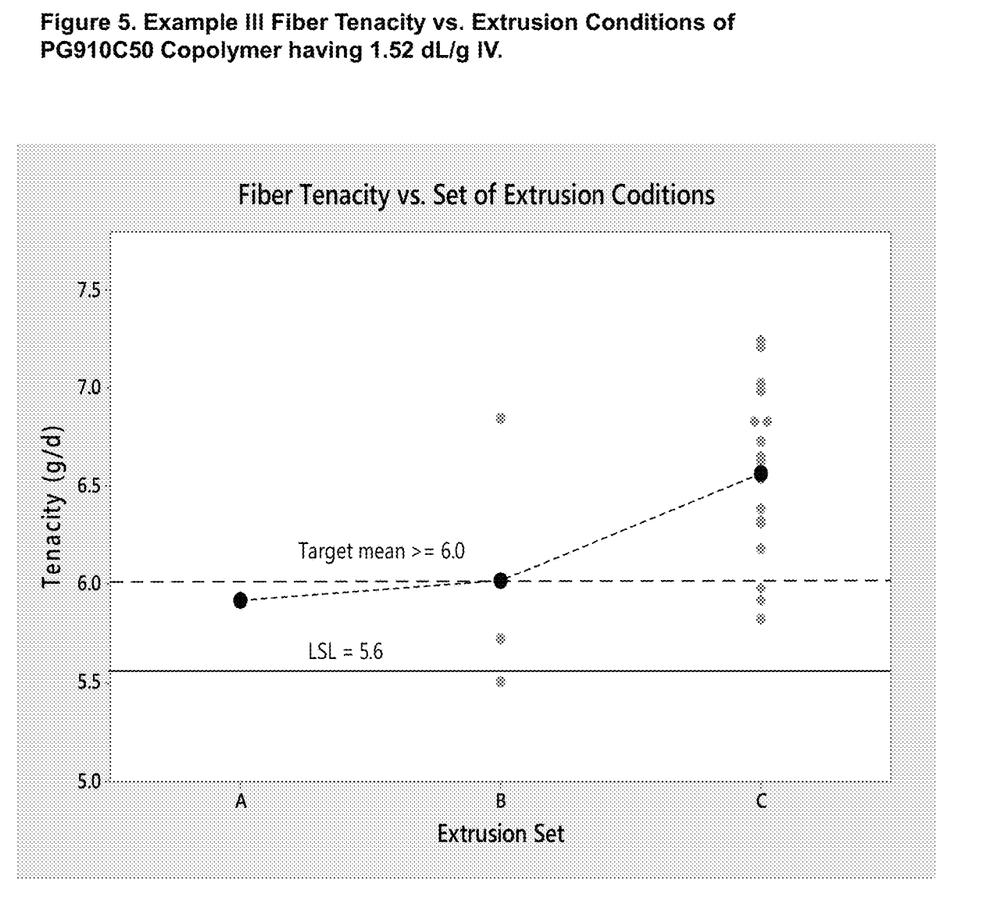
FIG. 5. Fiber Tenacity of Trial III Examples vs. Extrusion Conditions of PG910050 Copolymer having 1.52 dL/g IV.

As shown in the FIG. 5, most (except one) of the fiber samples made under both A and B conditions had individual spool average tenacity meeting the 5.6 gpd LSL and the mean tenacity was close but barely meeting the target minimum of 6.0 gpd. When the temperature in pump, block and spinneret zones dropped 5° C. in condition C, the individual spool average tenacity of all samples passed the 5.6 gpd LSL, and the mean tenacity increased noticeably to about 6.6 gpd, significantly above the proposed minimum target mean of 6.0 gpd.

The results of Trial III demonstrated that even with a relatively high IV block copolymer of PG910050, it is still preferable to keep the temperature in two or more of the extrusion zones at least 5° C. below the polymer melting point. The metering zone, pump and block zones should be no more than 20° C., more preferably no more than 15° C., above the polymer melting point. The spinneret temperature is preferably no more than 30° C. above the polymer melting point, which is to the contrary of the prior art teaching of at least 40° C. above the melting point as recommended in U.S. Pat. No. 7,378,045.

Braided Suture Examples

Fibers from examples of Trials I, II and III produced under the preferred process conditions of the current invention were used to make size 2-0 braided sutures for in vitro performance testing, which is designed and verified to predict the suture strength retention profile in vivo after implantation in an animal or human body.

The annealed 2-0 braids as described were placed in a buffer solution mimicking physiological conditions: 37° C. and neutral pH=7.27. Starting from day zero, the samples were removed from the physiological solutions every 7 days and subjected to Instron tensile properties examinations. Straight tensile strength was monitored as a function of hydrolysis time. The Instron Gauge speed was one inch per minute with the Gauge length of one inch. A 100-lb load cell was used. For the time zero, steel faces were used on the Instron machine, for all other hydrolysis times rubber faces were used to avoid slippage. After removing samples from the buffer baths, they could cool down (equilibrate) at room temperature, and then were all tested wet.

The suture properties including in vitro test are given in Table 9. For the application of wound closure that require extended support, the material specs for size 2-0 suture include a diameter in the range of 12.5-13.5 mils, a minimum initial tensile strength of 9.2 pounds, and a minimum breaking strength retention (BSR) of 2.3 pounds at 42 days post-implantation, and/or a minimum breaking strength retention of 10 percentages from the initial value at 42 days post-implantation.

TABLE 9

Properties of Size 2-0 Braided Suture using Fibers Produced with the Preferred Extrusion Conditions of the Invention

| Extrusion Trial | Sample Set | Polymer IV (dL/g) | Diameter (mils) | Annealed Braid Tensile (lbs) | Initial Strength (lbs at 0-day) | BSR at 42 days (lbs) | BSR (%) at 42 days |
|---|---|---|---|---|---|---|---|
| Required Specs: | | | 1.3-1.5 | 12.5-13.5 | ≥9.2 | ≥9.2 | ≥2.3 | ≥70 |
| I | D | 1.31 | 13.1 | 16.8 | 17.2 | 3.8 | 22.0 |
| I | F | 1.31 | 13.1 | 16.5 | 17.0 | 3.8 | 22.1 |
| II | D | 1.29 | 13.4 | 16.3 | 16.9 | 3.8 | 22.5 |
| II | E | 1.29 | 13.4 | 16.9 | 17.4 | 5.7 | 32.8 |
| III | B | 1.52 | 13.3 | 17.9 | 17.3 | 4.4 | 25.3 |
| III | C | 1.52 | 13.1 | 18.3 | 17.6 | 4.6 | 26.1 |

The results given in Table 9 showed that the suture samples made with both low and high IV PG910050 block copolymers under the preferred invention conditions have yielded initial tensile strength and the breaking strength retention (BSR) at 42 days post-implantation significantly exceeded the proposed finished goods specifications for USP size 2-0 suture having an average diameter of about 13 mils.

Although this invention has been shown and described with respect to detailed embodiments thereof, it will be understood by those skilled in the art that various changes in form and detail thereof may be made without departing from the spirit and scope of the claimed invention.

We claim:

1. A process for manufacturing a multifilament yarn with an extruder having at least a feeding zone, a transition zone and a metering zone, a pump and block section and a spinneret from an absorbable copolymer having a nominal average melting point into multifilament fibers comprising the steps of:
    a. Setting and maintaining at least two of the three extrusion zones selected from the group consisting of the feeding zone, the transition zone and the metering zone, at an operational temperature from about 50° C. below to about 2° C. below the nominal average melting point of the copolymer,
    b. Setting and maintaining the pump and block section at a pump temperature from about 15° C. below to no more than 25° C. above the nominal average melting point of the copolymer;
    c. Setting and maintaining the spinneret at a spin temperature from about 10° C. below to no more than 30° C. above the nominal average melting point of the copolymer, wherein the copolymer is a block copolyester of A-B-A type having about 50/50 mole % of Glycolide/Lactide in the center block and overall composition of about 90/10 mole % Glycolide/Lactide.

2. The process of claim 1, wherein the multifilament fibers have an individual spool average tenacity of at least 5.6 g/d.

3. A process for manufacturing a multifilament yarn with an extruder having at least a feeding zone, a transition zone and a metering zone, a pump and block section and a spinneret from an absorbable copolymer having a nominal average melting point into multifilament fibers comprising the steps of:
    a. Setting and maintaining at least two of the three extrusion zones selected from the group consisting of the feeding zone, the transition zone and the metering zone, at an operational temperature from about 50° C. below to about 2° C. below the nominal average melting point of the copolymer,
    b. Setting and maintaining the pump and block section at a pump temperature from about 15° C. below to no more than 25° C. above the nominal average melting point of the copolymer;
    c. Setting and maintaining the spinneret at a spin temperature from about 10° C. below to no more than 30° C. above the nominal average melting point of the copolymer, wherein the copolymer is a block copolyester of A-B-A type having about 50/50 mole % of Glycolide/Lactide in the center block and overall composition of about 90/10 mole % Glycolide/Lactide and wherein the block copolyester copolymer has an inherent viscosity (IV) in the range of 1.4-1.6 dL/g.

4. The A process for manufacturing a multifilament yarn with an extruder having at least a feeding zone, a transition zone and a metering zone, a pump and block section and a spinneret from an absorbable copolymer having a nominal average melting point into multifilament fibers comprising the steps of:
    a. Setting and maintaining at least two of the three extrusion zones selected from the group consisting of the feeding zone, the transition zone and the metering zone, at an operational temperature from about 50° C. below to about 2° C. below the nominal average melting point of the copolymer,
    b. Setting and maintaining the pump and block section at a pump temperature from about 15° C. below to no more than 25° C. above the nominal average melting point of the copolymer;
    c. Setting and maintaining the spinneret at a spin temperature from about 10° C. below to no more than 30° C. above the nominal average melting point of the copolymer, wherein the multifilament fibers have a lot mean tenacity of at least 6.0 g/d
    and
    wherein braided multifilament suture made from the multifilament fibers has a breaking strength retention of at least 10% at 42 days after implantation.

5. The process of claim 1 or claim 3 or claim 4, wherein at least two (2) of the three extrusion zones are maintained at temperatures at least 5° C. below the copolymer nominal average melting point.

6. The process of claim 4, wherein the copolymer is an absorbable copolyester possessing an overall composition of about 90/10 mole % Glycolide/Lactide.

7. The process claim 4, wherein the copolymer is a block copolyester of A-B-A type having about 50/50 mole % of Glycolide/Lactide in the center block and overall composition of about 90/10 mole % Glycolide/Lactide.

8. A process for manufacturing a multifilament yarn with an extruder having at least a feeding zone, a transition zone and a metering zone, a pump and block section and a spinneret from an absorbable copolymer having an inherent viscosity (IV) from 1.2-1.4 and a nominal average melting point into multifilament fibers comprising the steps of:
    a. Setting and maintaining at least two of the three extruder zones selected from the group consisting of the feeding zone, the transition zone and the metering zone, at an operating temperature from about 50° C. below to about 2° C. below the copolymer nominal average melting point,
    b. Setting and maintaining the pump and block section at a pump temperature from about 15° C. below, to about 3° C. below the copolymer nominal average melting point;
    c. Setting and maintaining the spinneret at a die temperature from about 8° C. below to no more than about 10° C. above the copolymer nominal average melting point, wherein the copolymer is an absorbable copolyester possessing an overall composition of about 90/10 mole % Glycolide/Lactide.

9. A process for manufacturing a multifilament yarn with an extruder having at least a feeding zone, a transition zone and a metering zone, a pump and block section and a spinneret from an absorbable copolymer having an inherent viscosity (IV) from 1.2-1.4 and a nominal average melting point into multifilament fibers comprising the steps of:
    a. Setting and maintaining at least two of the three extruder zones selected from the group consisting of the feeding zone, the transition zone and the metering zone, at an operating temperature from about 50° C. below to about 2° C. below the copolymer nominal average melting point, b. Setting and maintaining the pump and block section at a pump temperature from about 15° C. below, to about 3° C. below the copolymer nominal average melting point;

c. Setting and maintaining the spinneret at a die temperature from about 8° C. below to no more than about 10° C. above the copolymer nominal average melting point, wherein the copolymer is a block copolyester of A-B-A type having about 50/50 mole % of Glycolide/Lactide in the center block and overall composition of about 90/10 more Glycolide/Lactide.

10. A process for manufacturing a multifilament yarn with an extruder having at least a feeding zone, a transition zone and a metering zone, a pump and block section and a spinneret from an absorbable copolymer having an inherent viscosity (IV) from 1.2-1.4 and a nominal average melting point into multifilament fibers comprising the steps of:

a. Setting and maintaining at least two of the three extruder zones selected from the group consisting of the feeding zone, the transition zone and the metering zone, at an operating temperature from about 50° C. below to about 2° C. below the copolymer nominal average melting point, b. Setting and maintaining the pump and block section at a pump temperature from about 15° C. below, to about 3° C. below the copolymer nominal average melting point;

c. Setting and maintaining the spinneret at a die temperature from about 8° C. below to no more than about 10° C. above the copolymer nominal average melting point, wherein braided multifilament suture made from the multifilament fibers has a breaking strength retention of at least 10% at 42 days after implantation.

11. The process of claim 8 or claim 9 or claim 10, wherein at least three (3) of the extrusion zones are maintained at temperatures at least 5° C. below the polymer nominal average melting point.

12. The process of claim 8 or claim 9 or claim 10, wherein the multifilament fibers have an individual spool average tenacity of at least 5.6 g/d.

13. The process of claim 8 or claim 9 or claim 10, wherein the multifilament fibers have a lot mean tenacity of at least 6.0 g/d.

* * * * *